United States Patent [19]
Richardson et al.

[11] Patent Number: 5,653,372
[45] Date of Patent: Aug. 5, 1997

[54] APPARATUS FOR ORIENTING A FASTENER IN A CLASPING ARRANGEMENT

[76] Inventors: Thomas W. Richardson; Mary Jane Richardson, both of 7936 Madison St., Burr Ridge, Ill. 60521

[21] Appl. No.: 411,557

[22] Filed: Mar. 28, 1995

Related U.S. Application Data

[60] Division of Ser. No. 116,971, Sep. 7, 1993, abandoned, which is a continuation-in-part of Ser. No. 942,584, Sep. 9, 1992, Pat. No. 5,337,946.

[51] Int. Cl.$^6$ ................................................ B23P 11/00
[52] U.S. Cl. .................... 227/155; 227/110; 29/243.51
[58] Field of Search ............................ 227/110, 155, 227/107, 111; 29/243.51, 243.5

[56] References Cited

U.S. PATENT DOCUMENTS

| | | | |
|---|---|---|---|
| 180,181 | 7/1876 | Wineman | 411/491 |
| 1,029,574 | 6/1912 | Bell | 411/496 |
| 1,898,678 | 2/1933 | Maynard | 227/155 |
| 2,468,715 | 4/1949 | Numbers | 227/155 |
| 2,908,008 | 10/1959 | Potter | 29/243.51 |
| 3,261,085 | 7/1966 | Hobson | 29/243.51 |
| 3,581,350 | 6/1971 | McComb | 24/33 |
| 3,871,227 | 3/1975 | Tidwell, Jr. | 227/155 X |
| 3,900,144 | 8/1975 | Hamilton | 227/155 |
| 4,111,080 | 9/1978 | Pray | 29/243.51 |
| 4,194,666 | 3/1980 | Spehrley, Jr. et al. | 227/155 |
| 4,281,785 | 8/1981 | Brooks | 227/120 |
| 4,315,589 | 2/1982 | Soong | 227/155 |
| 4,333,217 | 6/1982 | Pray | 29/243.51 |
| 4,538,755 | 9/1985 | Schick | 29/243.51 X |
| 5,095,590 | 3/1992 | Schick | 24/33 |
| 5,178,314 | 1/1993 | Radtke et al. | 227/110 |
| 5,221,036 | 6/1993 | Takase | 227/19 |
| 5,337,946 | 8/1994 | Richardson et al. | 227/110 |
| 5,350,400 | 9/1994 | Esposito et al. | 227/902 X |

FOREIGN PATENT DOCUMENTS

WO83/00614  3/1983  WIPO.

*Primary Examiner*—Joseph J. Hail, III
*Assistant Examiner*—Jay A. Stelacone
*Attorney, Agent, or Firm*—Gerstman, Ellis & McMillin, Ltd.

[57] ABSTRACT

An apparatus for orienting a fastener in a clasping arrangement with a workpiece, the fastener presenting a first leg and a second leg joined by a bight intermediate the first leg and the second leg, comprises a deflector for engaging the first leg and the second leg. The deflector comprises a generally planar surface and a single cavity intersecting the surface in a substantially elliptical opening having a major axis and a minor axis. The cavity has at least a first interior wall and a second interior wall. The first wall slopes from the opening in a first direction toward a depth limit; the second wall slopes from the opening in a second direction toward the depth limit. The depth limit is substantially coincident with one of the first axis and the second axis. The deflector structure and the fastener interact when meeting in response to a driving force by the first leg being deflected along the first wall in the first direction and by the second leg being deflected along the second wall in the second direction.

18 Claims, 5 Drawing Sheets

FIG. 17

APPARATUS FOR ORIENTING A FASTENER IN A CLASPING ARRANGEMENT

This is a division of application Ser. No. 08/116,971, filed Sep. 7, 1993, now abandoned which is a continuation-in part of U.S. application Ser. No. 07/942,584, filed Sep. 9, 1992, now U.S. Pat. No. 5,337,946.

BACKGROUND OF THE INVENTION

The present invention is directed to a system for affixing a device to a workpiece, and is especially useful in effecting clinching fastener affixation, such as stapling, of a device to the end of a flexible belt for facilitating configuration of the belt as an endless belt.

Flexible endless belts connected with flexible steel fastening devices at the ends have been known for some time. In such products, there has long been and continues to be a need for a strong, reliable, flexible belt splice for splicing the two ends of the belt together to form an endless belt.

Belting fabrics and polymers have been improved over the years in terms of strength, stability, and reliability, but the staple fastenable belt splice device and its associated staple fastener tooling have not kept pace with the advances in belting fabrics and polymers. Basic problems with staples and their associated staple fastener tooling remain: staples are inconsistent in their clinching; staples experience a broken bridge or central portion intermediate their respective legs during installation; and staples are deflected off-line or out of their intended position.

Such problems require solutions in three major areas: staple design, staple driving device design, and design of a staple anvil to receive the staple and clinch it properly about a workpiece.

Generally available commercial staples used on belt splices are of two basic designs: a round wire design with rounded points and a flat wire design with chisel points.

It is desirable to have a system for establishing clinching affixation which is efficient for commercial production, will not provide a cutting edge on the belting or other workpiece to which the associated fastener is applied, will establish a fastening with sufficient strength to hold the respective fastener clinched to the workpiece under tension, and will be easy to operate. Thus, the staple design, the staple driving device, and the device to receive and deflect the staple to accomplish clinching should all be considered simultaneously.

SUMMARY OF THE INVENTION

The present invention is a system for affixing a device to a workpiece. The system comprises a dynamic fastener applicator for imparting motion to a fastener with respect to the workpiece by urging the fastener along a path so that the fastener piercingly encounters the workpiece and fixedly engages the device with the workpiece, and a static fastener applicator such as a fastener anvil for effecting clasping engagement of the workpiece and the device by the fastener. The static fastener applicator presents a deflecting structure in the path traveled by the driven fastener which orients the fastener to a clasping configuration for establishing the desired clasping engagement. The invention further comprises a positioning apparatus for precisely establishing desired relative positions of the workpiece, the dynamic fastener applicator, the static fastener applicator, and the device for the desired clasping engagement. The positioning apparatus includes a plurality of pins and a plurality of pin-positioning structures which cooperate to laterally situate the dynamic fastener applicator, the device, and the deflecting structure for appropriately effecting the desired clasping engagement. Proper alignment of the deflecting structure and driven fasteners, such as staples, reduces impact forces on staples, and thus reduces broken bridge portions of installed staples.

It is therefore an object of the present invention to provide a system for affixing a device to a workpiece which consistently effects clinching engagement of a fastener with the workpiece and the device.

A further object of the present invention is to provide a system for affixing a device to a workpiece which provides appropriate alignment of a fastening driver and a fastening anvil for effecting a desired clinching engagement between the device and a workpiece.

Yet a further object of the present invention is to provide a system for affixing a device to a workpiece which is easy and efficient in its operation.

Further objects and features of the present invention will be apparent from the following specification and claims when considered in connection with the accompanying drawings illustrating the preferred embodiment of the invention.

DETAILED DESCRIPTION OF THE INVENTION

Figure 1:
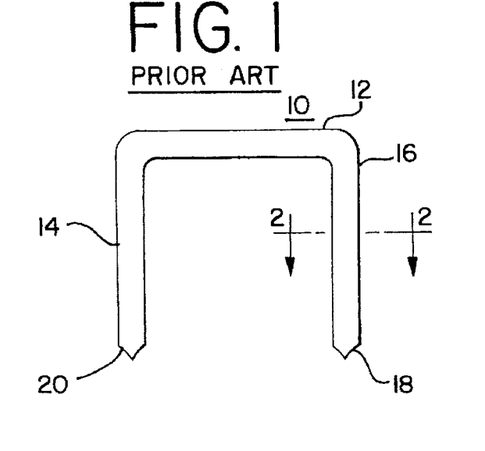
FIG. 1 is a plan view of a round staple with a round point.

FIG. 1 is a plan view of a round staple with a round point. In FIG. 1, a round wire staple 10 is illustrated comprising a bight 12 connecting a first leg 14 and a second leg 16.

Figure 2:
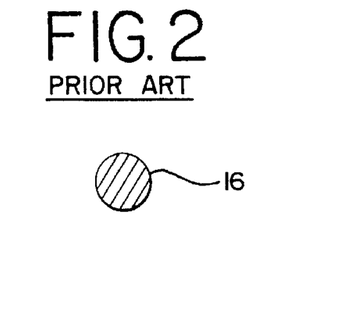
FIG. 2 is a section view of FIG. 1 taken along section line 2—2 of FIG. 1.

FIG. 2 is a section view of FIG. 1 taken along section line 2—2 of FIG. 1. In FIG. 2, leg 16 is illustrated as being round in cross section and, referring to FIG. 1, terminates in a round point 18. Leg 14 terminates in a round point 20. A round point minimizes cutting of a workpiece during installation, but a round point is expensive to manufacture and therefore is not a commercially feasible alternative.

Figure 3:
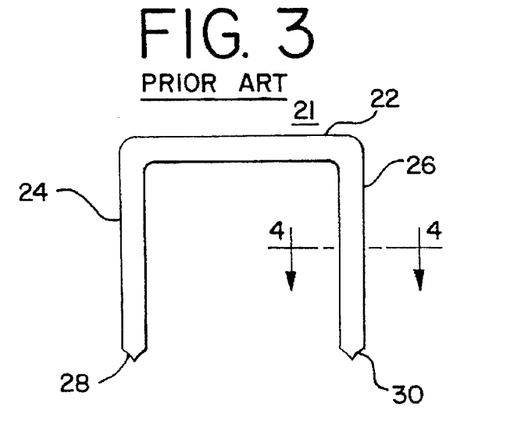
FIG. 3 is a plan view of a flat staple with chisel points.

FIG. 3 is a plan view of a flat staple with chisel points. In FIG. 3, a flat wire staple 21 is illustrated comprising a bight section 22 interconnecting a first leg 24 and a second leg 26. First leg 24 and second leg 26 terminate in chisel points 28, 30.

Figure 4:
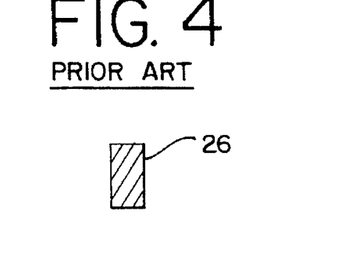
FIG. 4 is a section view of the staple of FIG. 3 taken along section line 4—4 of FIG. 3.

FIG. 4 is a section view of the staple of FIG. 3 taken along section line 4—4 of FIG. 3. In FIG. 4, second leg 26 of flat wire staple 21 is illustrated as being generally rectangular in cross section. A flat wire stale with chisel points such as staple 21 is cheaper to produce than a round wire staple with rounded points, but such a flat wire staple acts much as a knife and cuts a belt when the belt is subjected to operating tension.

Figure 5:
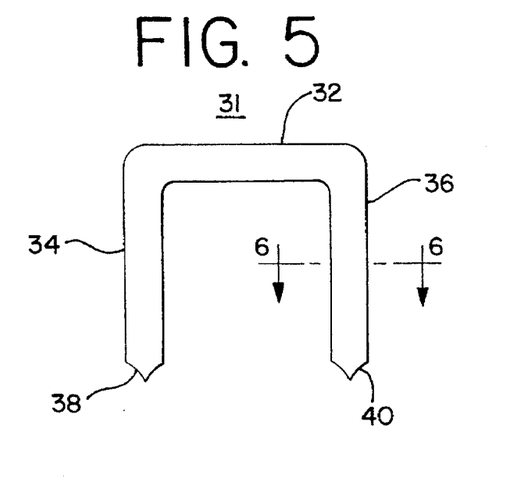
FIG. 5 is a plan view of an oval staple with a chisel point.

FIG. 5 is a plan view of an oval staple with a chisel point. In FIG. 5, oval wire staple 31 is illustrated comprising a bight section 32 intermediate a first leg 34 and a second leg 36. Legs 34, 36 terminate in chisel points 38, 40.

Figure 6:
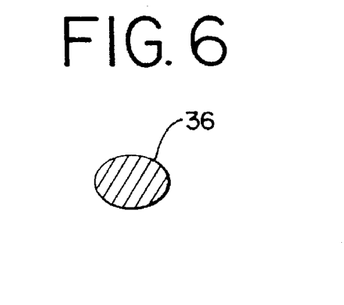
FIG. 6 is a section view of the staple of FIG. 5 taken along line 6—6 of FIG. 5.

FIG. 6 is a section view of the staple of FIG. 5 taken along line 6—6 of FIG. 5. In FIG. 6, leg 36 is illustrated as being oval in cross section. The inventor has discovered that an oval wire with rounded edges provides an optimum staple. Its oval cross section provides greater strength than a round wire cross section, and the smooth edges of the oval wire do not act as cutting wedges with the belt under tension as is the case with flat wire staples.

The point of the staple is also extremely important. Various designs are available: round, slash, blunt, and chisel. A blunt point acts as a punch, cuts the fabric of the belt fabric to which it is applied and weakens the belt.

Slash points and chisel points penetrate a workpiece without destroying the belt fabric. Each of those points are easily made and collated for dispensing on a staple driver. However, a slash point does not generally drive straight. As a staple is driven through a belt or other workpiece, it meets resistance and as the staple point reaches the device intended to clinch the staple (i.e., the anvil), it meets further resistance. The shape of the slash point causes the staple to experience unequal resistance on two opposing sides during driving, thus causing the staple to travel off-line. Such off-line travel can cause the staple to contact the belt splice device or to improperly contact the anvil, thus resulting in improper clinching by the staple.

A chisel point staple, having a 45° central angle with equal legs on each side of the point, has been found to drive straight through belt fabric without deflecting since equal resistance by the belt is encountered on both sides of each point. Further, the 45° angle separates the belt material as it penetrates so that minimal cutting or destruction of the fabric results. Still further, as the 45° angle meets the angle of the device used to clinch or bend the staple (i.e., the staple anvil), the staple bends in the desired clinch configuration more reliably and more repeatably.

Figure 7:
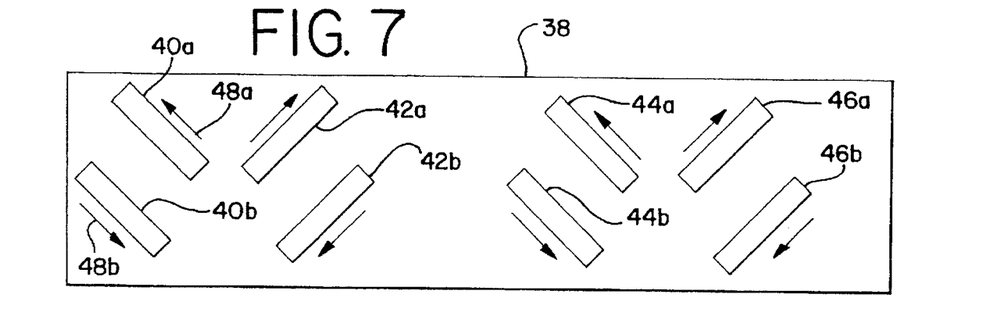
FIG. 7 is a plan view of an array of staple bending cavities in a fastener anvil.

FIG. 7 is a plan view of an array of staple bending cavities in a fastener anvil. In FIG. 7, a fastener anvil 38 presents a plurality of cavities arranged in pairs: 40a, 40b; 42a, 42b; 44a, 44b; 46a, 46b. Each respective pair of cavities (for example, cavities 40a, 40b) are configured to receive legs of a fastener, such as a staple, and to direct those received legs in opposing directions substantially parallel in orientation. This is, cavity 40a and cavity 40b each receives a leg of a staple; cavity 40a directs the staple leg received therein in the direction indicated by arrow 48a and cavity 40b directs the leg of the staple received therein in the direction indicated by the arrow 48b.

A longer leg on a staple is easier to bend than a shorter leg to achieve the desired clinching relationship about a workpiece. However, there is difficulty in having too long a leg on a staple if the legs overlap each other when bent in the desired clinching orientation. Such an overlapping orientation is not desirable in such applications as an endless conveyor belt since the overlapping staples interfere with smooth travel of the splice over rollers or other guides in a conveyor system. Thus, it is desirable that the staple anvil provides cavities for reorienting, or directing, driven staples appropriately to establish a proper bending angle while also providing that the two legs do not overlap. Such a result in established by providing that the bent staple legs bypass each other in generally parallel, oppositely directed arrangement.

Proper alignment of the staples with the staple anvil during application of the staples is important in order to effect such a desired clinching arrangement among the staples, the device to be attached to the workpiece (i.e., the splicing device), and the workpiece (i.e., the belting). It is important to precisely and repeatably locate the device to be attached to the belt (in the case of a continuous conveyor, the device is generally in the form of a fastener strip substantially traversing the end of the conveyor belt) with respect to the cavity in the staple anvil that will bend the legs of the staple, and to simultaneously precisely and repeatably locate the staple driver (and, hence, the path of travel of a driven staple), with respect to the staple anvil.

Figure 8:
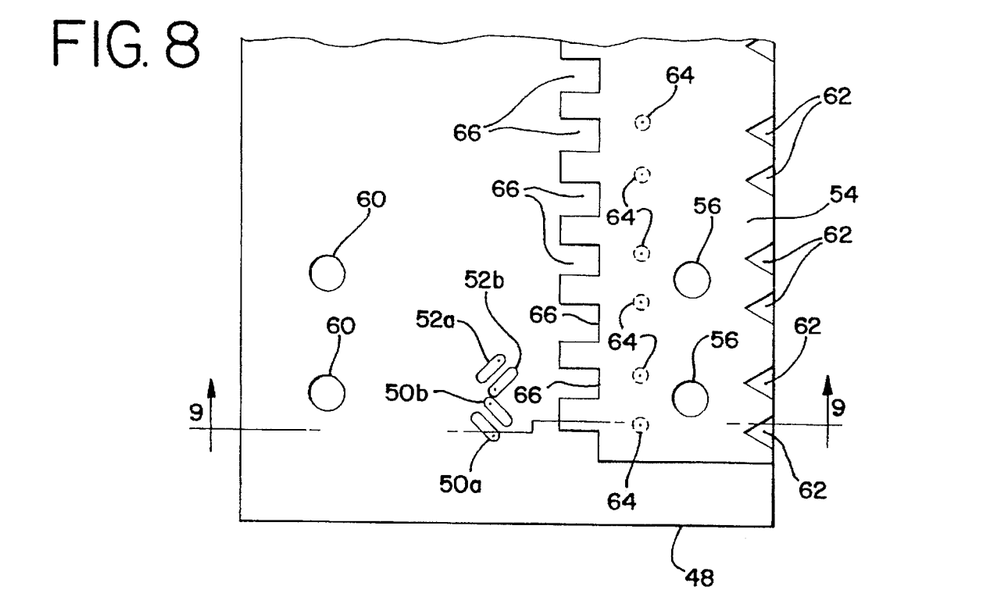
FIG. 8 is a plan view of the preferred embodiment of the template of the present invention associated with a staple anvil.

FIG. 8 is a plan view of the preferred embodiment of the template of the present invention associated with a stapler anvil. In FIG. 8, a stapler anvil 48 is illustrated presenting a plurality of pairs of staple cavities 50a, 50b; 52a, 52b. A top plate of template 54 is affixed to a stapler anvil 48 via dowels or screws 56, 60.

Figure 9:
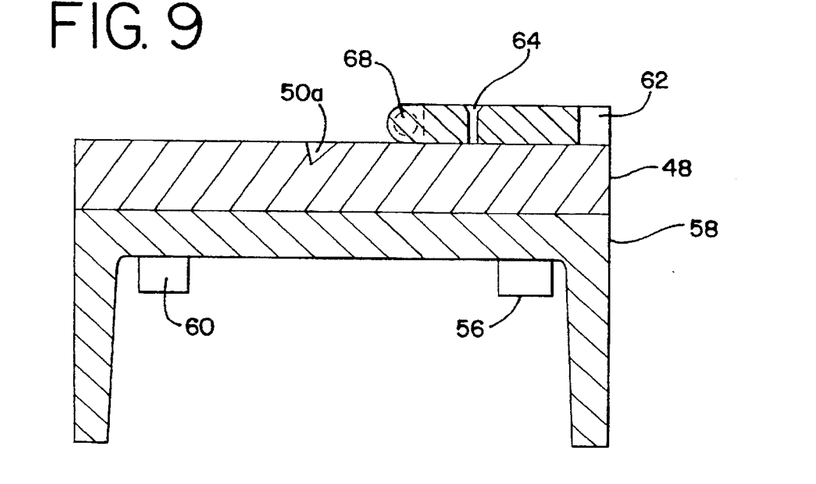
FIG. 9 is a side section view of the apparatus illustrated in FIG. 8 taken along line 9—9 of FIG. 8.

FIG. 9 is a side section view of the apparatus illustrated in FIG. 8, taken along line 9—9 of FIG. 8. In FIG. 9, stapler anvil 48 is seen as being affixed to a base or table 58 via dowels or screws 56, 60, which also affix template 54 to staple anvil 48. Template 54 presents preferably V-shaped guide slots 62 and alignment apertures 64 for aligning a staple applicator, as will be described hereinafter. Template 54 also presents fastener device accommodating slots 66 for aligningly engaging fasteners to be affixed to the end of a workpiece appropriately for installation on the workpiece via clinching fasteners, such as staples. The staples (not shown in FIGS. 8–9) are driven through the workpiece, through the fastener device, and into the stapler cavities, as will be described hereinafter. Referring to FIG. 9, it may be seen that an alignment aperture 68 is associated with fastener guidance slot 66.

Figure 10:
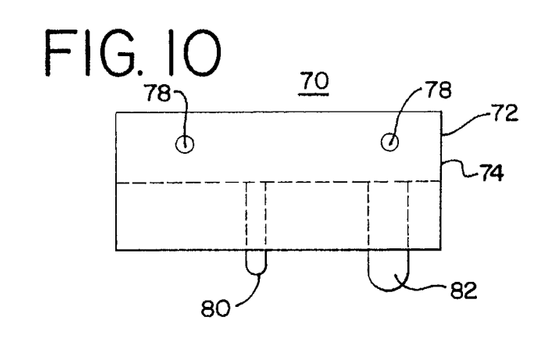
FIG. 10 is a side view of the preferred embodiment of a positioning apparatus for use with a staple driver.
Figure 11:
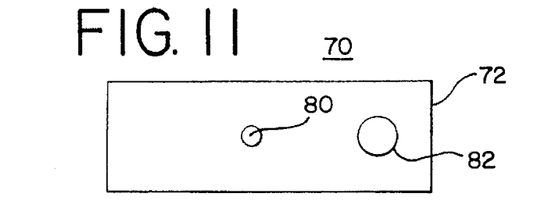
FIG. 11 is a bottom view of the positioning apparatus illustrated in FIG. 10.
Figure 12:
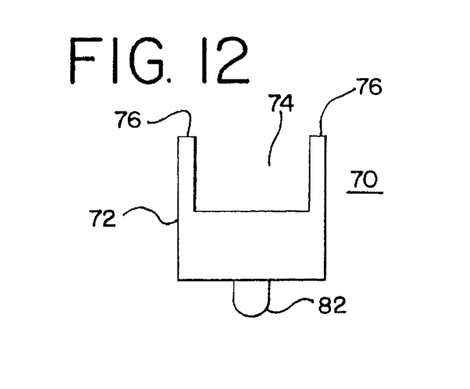
FIG. 12 is an end view of the positioning apparatus illustrated in FIG. 10.
Figure 13:
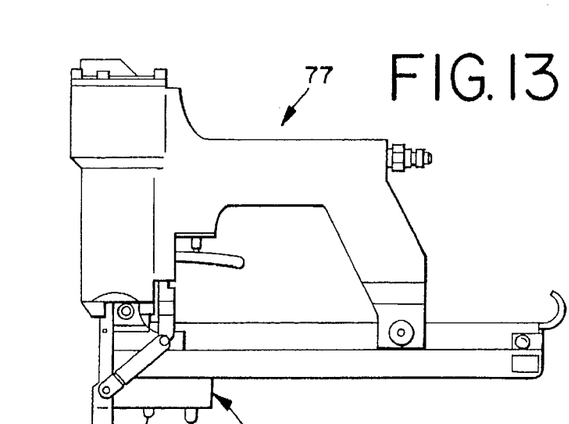
FIG. 13 is an illustration of a representative staple driver with the positioning apparatus of FIGS. 10–12 installed thereon.

FIG. 10 is an end view of the preferred embodiment of a positioning apparatus for use with a staple driver. FIG. 11 is a bottom view of the positioning apparatus illustrated in FIG. 10. FIG. 12 is a side view of the positioning apparatus illustrated in FIG. 10. FIG. 13 is an illustration of a representative staple driver with the positioning apparatus of FIGS. 10–12 installed thereon.

In FIGS. 10–13, a positioning apparatus 70 is illustrated comprising a generally U-shaped block 72 presenting a channel 74 bound by legs 76. Mounting holes 78 are presented in order that positioning apparatus 70 may be mounted to a stapling apparatus 77, as illustrated generally in FIG. 13. Guidance pins 80, 82 are presented by positioning apparatus 70 and project downward from positioning apparatus 70 when positioning apparatus 70 is installed on a stapling apparatus 77 as indicated generally in FIG. 13.

Thus, positioning stapling apparatus 77 for fastening a device, a workpiece, and a clinching fastener such as a staple, employing a stapler anvil 48 (FIG. 8) may be accomplished with the preferred embodiment of the present invention by positioning guidance pin 82 within a respective guide slot 62 and positioning guidance pin 80 in an associated alignment aperture 64 appropriately to align the thus laterally-positioned stapling apparatus 77 over appropriate staple cavities 50a, 50b in staple anvil 48 (see FIG. 8).

Figure 14:
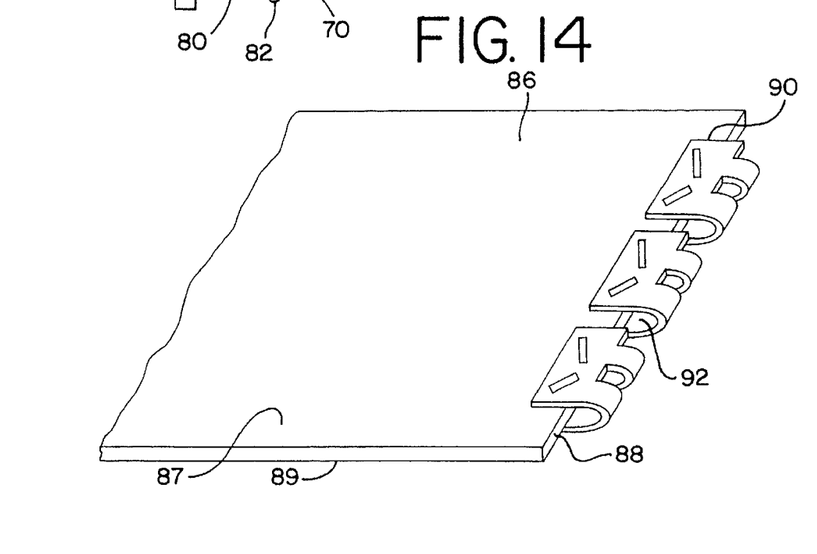
FIG. 14 is a perspective view of one end of a workpiece with fastener devices in place for creating an endless belt.

FIG. 14 is a perspective view of one end of a workpiece with fastener devices in place for creating an endless belt.

FIG. 14 illustrates the alignment of the various components associated with the fastening sought to be accomplished by the apparatus of the present invention. In FIG. 14, a workpiece, or belt, 86 has attached to an end 88 thereof a plurality of fasteners 90. Each fastener 90 presents a through-channel 92 which is oriented to nestingly receive complementary fasteners (not shown) on the other end of the same workpiece 86 so that passing a retaining pin (not shown) through complementary-aligned through-channels 92 linkingly joins fasteners 90 at the two ends of workpiece 86, thereby forming a continuous belt. The alignment of fasteners 90 with respect to workpiece 86, and alignment of fasteners 90 with appropriate staple cavities 50a, 50b of stapler anvil 48 is effected by insertion of the respective fasteners 90 in fastener guidance slots 66 of template 54, alignment of through-channels 92 with alignment aperture 68 and insertion of a retaining pin (not shown) through alignment aperture 68 in the various thus-aligned through-channels 92 to laterally position fasteners 90 with respect to stapler anvil 48. Thus, alignment of the stapling apparatus 77 via interaction of guidance pins 80, 82 with an appropriate guide slot 62 and an appropriate alignment aperture 64 of template 54 serves to laterally align stapling apparatus 77 for driving staples through fasteners 90, through workpiece 86, and encountering stapler anvil 48 appropriately at staple cavities 50a, 50b for staple cavities 50a, 50b to each receive a leg of the driven staple and redirect the legs of such driven staples to establish a desired clinching engagement affixing a fastener 90 to workpiece 86.

Figure 15:
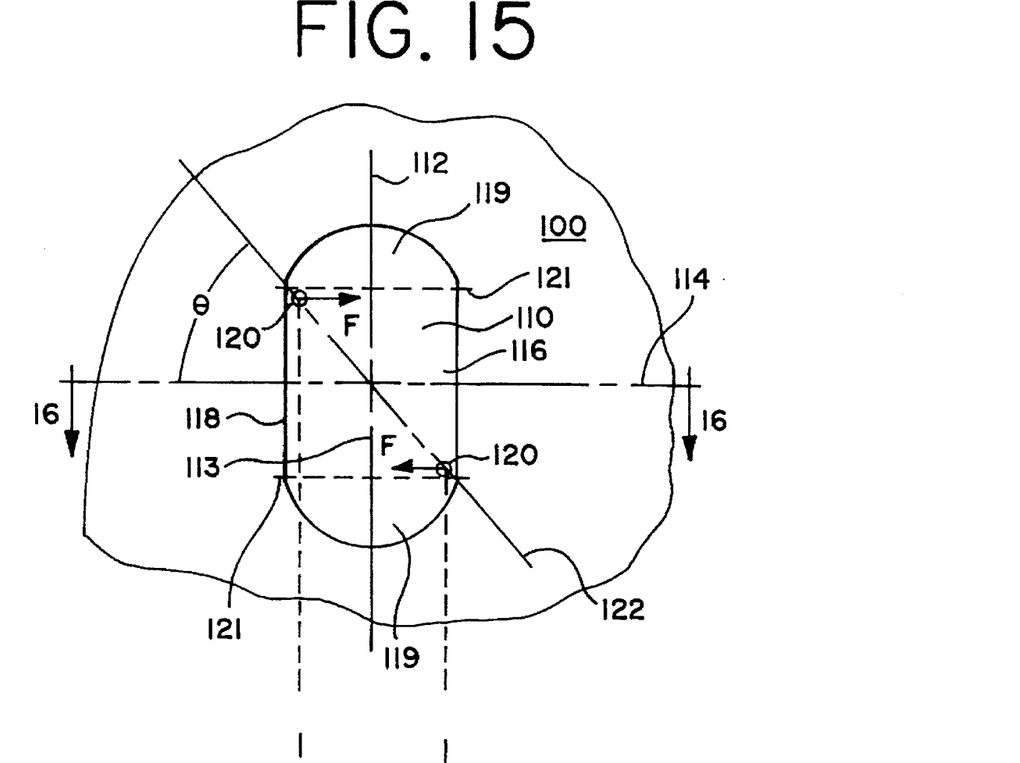
FIG. 15 is a plan view of the preferred embodiment of the present invention.

FIG. 15 is a plan view of the preferred embodiment of the present invention. In FIG. 15, an apparatus 100 for orienting a fastener (not shown) in a clasping engagement with a workpiece (not shown) is illustrated as comprising a deflector structure 110 in a form of a cavity. Deflector structure or cavity 110 is generally arranged along a major axis 112 and a minor axis 114. Cavity 110 presents sloping sides 116 which slope generally from an edge 118 of cavity 110 toward a maximum depth line 113 located substantially at major axis 112.

Cavity 110 also presents sloping ends 119 which slope generally from edge 118 toward a maximum depth line 121 for the end surface. In the preferred embodiment of the present invention, each sloping end wall 119 defines a generally spherical surface section and depth limit line 121 appears substantially diametrically oriented with respect to that spherical surface in FIG. 15, but actually line 121 follows the spherical, peripheral surface where end 119 joins sloping sides 116. Of course, sloping end 119 can define other surfaces than spherical surfaces; what is important is that substantially intersecting depth limit lines, such as lines 113, 121, are established which substantially define a deflection path for legs 120 of a fastener which is driven into cavity 110, as will be described in greater detail below.

Thus, line 121 defines a junction line between the spherical surfaces of ends 119 and the central portion of the recess which defines the sloping lateral sides 116.

Figures 16A, 16B:
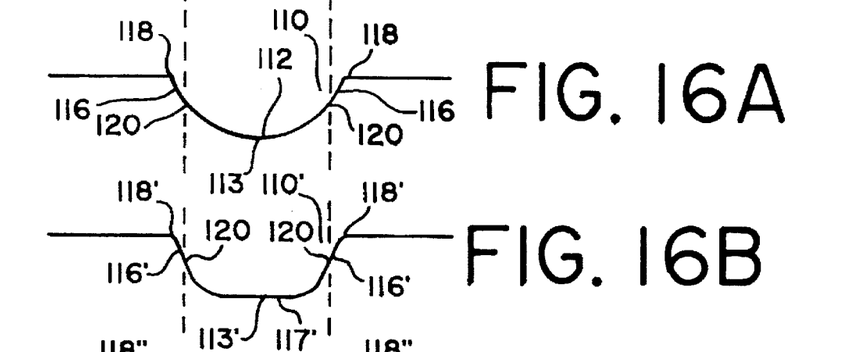
FIGS. 16(a)–(c) illustrate alternate representative section views of the preferred embodiment of the present invention taken along section line 16—16 at FIG. 15.
Figure 16C:
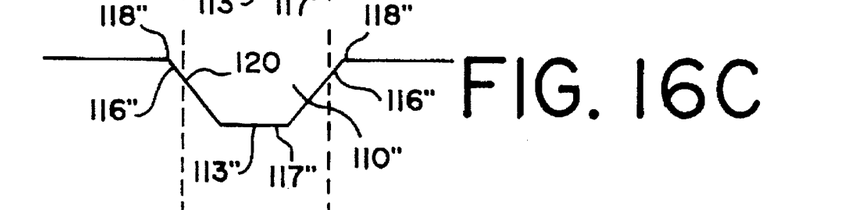

FIG. 16 illustrates alternate representative section views of the preferred embodiment of the present invention taken along section 16—16 of FIG. 15. In FIG. 16(a) cavity 110 is illustrated as having a generally semi-circular cross section presenting sloping sides 116 sloping from edge 118 toward depth limit line 113 substantially at major axis 112. In FIG. 16(b) cavity 110' is illustrated as presenting sloping sides 116' sloping from edge 118' toward depth limit area 113', with cavity 110' presenting a flat bottom portion 117'. In FIG. 16(c) cavity 110" is illustrated as presenting substantially linear sloping slides 116" sloping from edge 118" toward depth limit line 113', with cavity 110" presenting a flat bottom portion 117".

Of course, any of a wide variety of cross-sectional shapes of cavity 110 will suffice for the purposes of the present invention as will be understood in view of the detailed description of operation of the invention in conjunction with a fastener presented below. As long as sides 116 slope from an edge 118 toward a depth limit 113, and as long as depth limits 121 (FIG. 15) cooperate with sides 116 to define a deflection path for a fastener driven into cavity 110, the particular cross section of cavity 110, while affecting performance of a fastening operation, will not affect the completion of the fastening operation.

Referring to FIG. 15 and FIG. 16 together, the impact points 120 of two tines of a fastener, such as a staple, are illustrated on sloping sides 116, substantially at depth limits 121 adjacent sloping ends 119. The fastener (not shown) is preferably of a staple design substantially as shown in FIGS. 1–6. Thus, the legs of the staple, and, hence, the impact points 120 lie substantially in a plane 122. Plane 122 is offset from minor axis 114 by an offset angle Θ. By such angular displacement Θ of plane 122 from minor axis 114, impact points 120 are linearly displaced from minor axis 114. Consequently, as the fastener is driven into cavity 110 in a direction substantially perpendicular to major axis 112 and minor axis 114, the legs of the fastener, after impacting impact points 120, will be deflected and collapsed generally parallel to bight 12, 22, or 32, but also moving along interior sloping walls 116 and sloping ends 119 generally along a deflection path defined by depth limits 121 in the direction of arrows F in FIG. 15. In such manner, the respective legs of the fastener may be bent to establish a clasping engagement with a workpiece through which the fastener may have been forcibly passed by impact in a manner similar to the manner previously described in connection with other embodiments of the present invention with the respective legs in a generally parallel, oppositely directed orientation.

Cavity 110, with its single cavity to accommodate both tines of a staple fastener, and with its sloping interior walls 116 and sloping ends 119 sloping from edge 118 toward depth limits 113, 121, lends itself to a simpler manufacturing process and, therefore, results in a stapler anvil design which is more cheaply and more reliably manufacturable. In previous stapler anvil designs, such as the stapler anvil design illustrated in FIG. 7, each leg of each staple was provided an individual cavity for deflection while being driven. In this new improved stapler anvil design, the generally angular or curved interior of cavity 110 receives and deflects staples, tines or legs. Especially when staples for use with the present invention have a chisel point (the preferred fastener structure), the angular interaction of the staple point and sloping walls 116 of cavity 110 urge the staple along a deflection path within cavity 110 causing the legs of the staple to bypass each other in an oppositely directed, generally parallel orientation, as described above. Of course, the present invention may be used with staples having points other than chisel points. A preferred value for offset angle Θ is approximately 60 degrees to effectively accomplish the desired parallel oppositely directed orientation of the legs of the staple when staple driving is complete.

Figure 17:
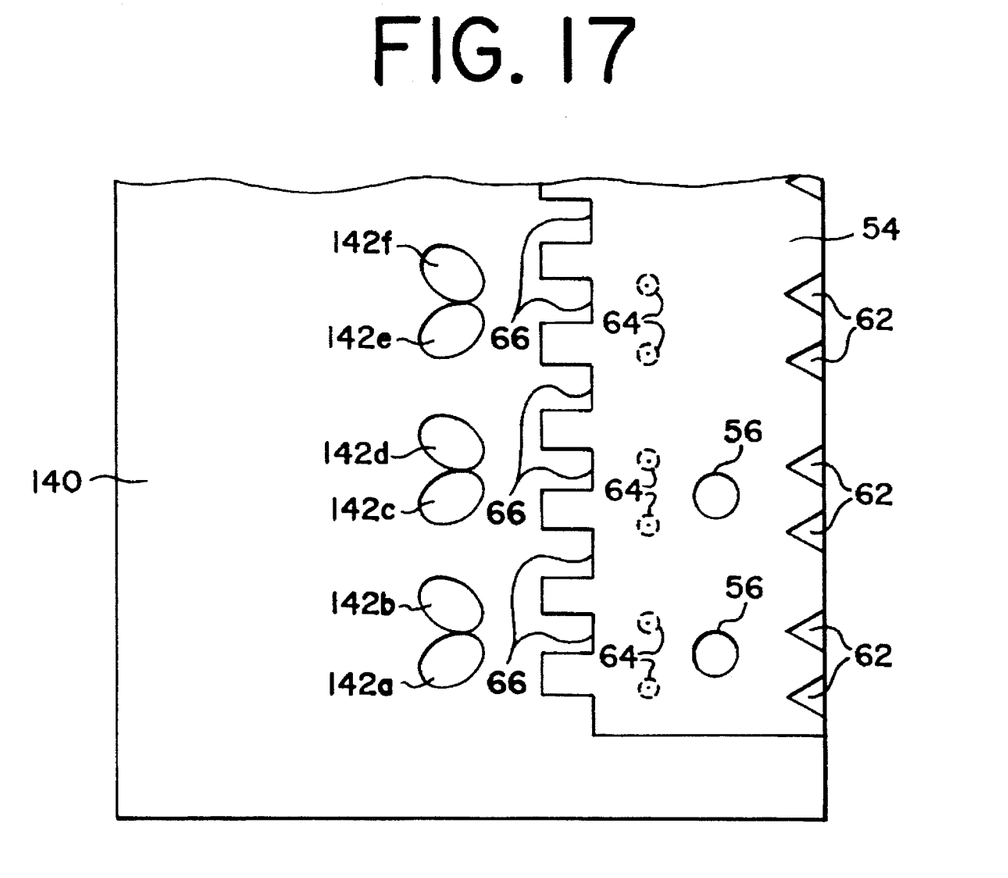
FIG. 17 is a plan view of an employment of a plurality of the present invention in a system for affixing a device to a workpiece.

FIG. 17 is a plan view of an employment of a plurality of cavities of the present invention in a system for affixing a device to a workpiece. In FIG. 17, a fastener anvil 140 presents a plurality of cavities 142a, 142b, 142c, 142d, 142e, 142f. Each respective individual cavity 142 is configured to receive both legs of a fastener, such as a staple, and to direct those received legs generally in a substantially parallel and oppositely directed orientation as previously described in connection with FIG. 15 and FIG. 16. Adjacent staples may thus be emplaced parallel to each other because of the acute angle relation of pairs of cavities 142a, 142b, etc. A top plate or template 54 fixed to stapler anvil 140 via dowels or screws 56 and having guide slots 62, alignment apertures 64, and fastener device accommodating slots 66 operates substantially the same as template 54 described in connection with FIG. 8 to align a staple driving device with stapler anvil 140.

Thus, as described above, one can emplace a wire fastener by bending the fastener with the wire fastener comprising a linear bight and a pair of spaced, substantially parallel legs extending transversely from the bight, with the legs having free ends. The method used comprises the steps of positioning the free ends of both of the legs against an anvil within at least one recess of the anvil and near edges of the recess. The recess defines sidewalls that slope inwardly from the edges to a recess bottom. The recess has a maximum depth that is substantially less than the length of the legs. The recess has a major axis and a minor axis perpendicular to the major axis, with the two axes being substantially greater in length than the width of the wire of the fastener. The fastener bight is positioned at an acute angle of both the major and minor axes of the recess or recesses.

By the method of this invention, one presses the fastener toward the anvil with the legs in one or both recesses to cause the legs to bend generally toward each other. The inwardly sloping sidewalls create a lateral component, relative to the bight, to the bending of the legs, which bending components of the legs are in opposite directions.

Preferably, the recess also defines inwardly sloping end walls to urge the legs of the wire fastener to begin inward bending as the fastener is pressed against the anvil.

In one embodiment as shown in FIG. 17, wire fasteners may be emplaced by pressing the legs of the fasteners each into a separate recess of a pair of recesses or cavities 142a, 142b for example. Thus, a plurality of staples may be applied through interaction with separate recess pairs 142. Since the major axis of each recess for cavity 142 shown defines an acute angle to the major axis of its companion cavity, the fasteners may be emplaced in substantially parallel relation to each other since their emplacement angle occupies an acute angle to each of the axes of the respective recesses.

In summary, the apparatus of this invention comprises (1) an anvil which in turn comprises a flat surface defining a recess of elongated shape having a major and minor axis perpendicular to each other and having sides that slope inwardly to a maximum depth. (b) a stapling apparatus is also provided for driving the legs of the staples against the opposed, sloped sides of the recess while the staple is held at an acute angle to both the major and the minor axes.

It is to be understood that, while the detailed drawings and specific examples given describe a preferred embodiment of the invention, they are for the purpose of illustration only, that the apparatus of the invention is not limited to the precise details and conditions disclosed and that various changes may be made therein without departing from the spirit of the invention which is defined by the following claims.

That which is claimed:

1. An apparatus for applying staples to a workpiece, which comprises:

an anvil which comprises a flat surface defining a at least one recess of elongated shape having a major and a minor axis perpendicular to each other, and having opposed sides that slope inwardly to a maximum depth, and a stapling apparatus for driving legs of staples against said opposed, sloped sides while the staple is held at an acute angle to the minor axis of substantially 45° to 60°.

2. The apparatus of claim 1 in which each said recess also defines inwardly sloping end walls.

3. The apparatus of claim 1 in which the at least one recess of said anvil comprises at least one pair of oval recesses, the major axis of each oval recess defining an acute angle to the major axis of the other recess of the pair, whereby said staples may be emplaced in substantially parallel relation.

4. The apparatus of claim 1 in which each said elongated recess is substantially oval.

5. The apparatus of claim 4 in which each said substantially oval recess defines end walls of substantially spherical shape, a portion of said recess extending between said end walls being of substantially cylindrical shape.

6. The apparatus of claim 5 in which the at least one recess of said anvil defines at least one pair of oval recesses, the major axis of each oval recess defining an acute angle to the major axis of the other recess of the pair.

7. The apparatus of claim 6 in which each substantially oval recess defines end walls of substantially spherical shape, a portion of said recess extending between said end walls being of substantially cylindrical shape.

8. The apparatus of claim 1 in which the staple had an oval cross section.

9. The apparatus of claim 1 which carries a staple of oval cross-section.

10. An apparatus for applying staples to a workpiece, which comprises:

an anvil which comprises a flat surface defining at least one pair of oval recesses, each recess having a major and a minor axis perpendicular to each other and having opposed sides that slope inwardly to a maximum depth, the major axis of one oval recess of each pair defining an acute angle to the major axis of the other recess of the same pair, and a stapling apparatus for driving legs of staples against said opposed, sloped sides of each said pair of recesses while each staples are held at an acute angle to both said major and minor axes, whereby said staples being driven against the opposed, sloped sides of the recesses of said pair may be emplaced in substantially parallel relation to each other.

11. The apparatus of claim 10 in which each said recess also defines inwardly sloping end walls.

12. The apparatus of claim 11 in which each substantially oval recess defines end walls of substantially spherical shape, a portion of each said recess extending between said end walls being of substantially cylindrical shape.

13. The apparatus of claim 12 in which the acute angle of each staple to the minor axis is substantially 45° to 60°.

14. The apparatus of claim 10 which carries a staple of oval cross-section.

15. An apparatus for applying staples to a workpiece, which comprises:

an anvil which comprises a flat surface defining at least a pair of recesses of substantially oval shape, said oval recesses each having a major and a minor axis perpendicular to each other, and having opposed sides that slope inwardly to a maximum depth, said substantially oval recesses further defining end walls of substantially spherical shape, a portion of each said recess extending between said end walls being of substantially cylindrical shape, the major axis of each oval recess of said pair defining an acute angle to the major axis of the other oval recess of said pair, and a stapling apparatus for driving legs of staples against said opposed sloped sides of said recess, while each staple is held at an acute angle to both said major and minor axes.

16. The apparatus of claim 15 which carries a staple of oval cross-section.

17. The apparatus of claim 16 in which the acute angle of each staple to the minor axis is substantially 45° to 60°.

18. The apparatus of claim 17 in which said staples driven into said pair of recesses are emplaced in substantially parallel relation.

* * * * *